US009334526B2

(12) United States Patent
Pavlov et al.

(10) Patent No.: US 9,334,526 B2
(45) Date of Patent: May 10, 2016

(54) METHOD FOR THE PRODUCTION OF HUMAN THROMBIN AND USES THEREOF

(71) Applicant: ASOCIACIÓN CENTRO DE INVESTIGACIÓN COOPERATIVA EN BIOMATERIALES—CIC BIOMAGUNE, San Sebastián, Guipúzcoa (ES)

(72) Inventors: Valery Pavlov, Guipúzcoa (ES); Laura Saa Peña, Guipúzcoa (ES); Ana Virel Sánchez, Guipúzcoa (ES)

(73) Assignee: ASOCIACION CENTRO DE INVESTIGACION COOPERATIVA EN BIOMATERIALES-CIC, San Sebastian, Guipuzcoa (ES)

( * ) Notice: Subject to any disclaimer, the term of this patent is extended or adjusted under 35 U.S.C. 154(b) by 67 days.

(21) Appl. No.: 14/355,079

(22) PCT Filed: Oct. 31, 2012

(86) PCT No.: PCT/EP2012/071572
§ 371 (c)(1),
(2) Date: Apr. 29, 2014

(87) PCT Pub. No.: WO2013/064542
PCT Pub. Date: May 10, 2013

(65) Prior Publication Data
US 2014/0322736 A1 Oct. 30, 2014

Related U.S. Application Data

(60) Provisional application No. 61/555,763, filed on Nov. 4, 2011.

(51) Int. Cl.
C12N 9/00 (2006.01)
C12N 15/00 (2006.01)
C12Q 1/56 (2006.01)
C12N 9/74 (2006.01)

(52) U.S. Cl.
CPC .............. C12Q 1/56 (2013.01); C12N 9/6429 (2013.01); C12Y 304/21005 (2013.01); C07K 2319/21 (2013.01)

(58) Field of Classification Search
CPC .................................. C12N 15/00; C12N 9/00
USPC ............................................ 530/350; 435/6.1
See application file for complete search history.

(56) References Cited

PUBLICATIONS

Lawson, J.H., "The clinical use and immunologic impact of thrombin in surgery," Seminars in Thrombosis and Hemostatis, 2006, pp. 98-110, vol. 32.
Heffernan, J.K., et al., "Preclinical safety of recombinant human thrombin," Regulatory Toxicology and Pharmacology, 2007, pp. 48-58, vol. 47.
Doyle, Margaret F., et al., "Multiple Active Forms of Thrombin. IV. Relative Activities of Meizothrombins," The Journal of Biological Chemistry, 1990, pp. 10693-10701, vol. 265.
Dibella, Elsie E., et al., "Expression and Folding of Recombinant Bovine Prethrombin-2 and Its Activation to Thrombin," The Journal of Biological Chemistry, 1995, pp. 163-169, vol. 270.
Yonemura, H., et al., "Preparation of recombinant alpha-thrombin: High-level expression of recombinant human prethrombin-2 and its activation by recombinant ecarin," Journal of Biochemistry, 2004, pp. 577-582, vol. 135.
Pötzsch, B., et al., "Monitoring of recombinant hirudin: assessment of a plasma-based ecarin clotting time assay," Thrombosis Research, 1997, pp. 373-383, vol. 86.
Fujikawa, Kazuo, et al., "Bovine factor X (Stuart factor)", Methods in Enzymology, 1976, pp. 89-95, vol. 45.
Zhu, L., et al., "Bienzymatic glucose biosensor based on co-immobilization of peroxidase and glucose oxidase on a carbon nanotubes electrode," Biosensors & Bioelectronics, 2007, pp. 528-535, vol. 23.
Nakamura, H., et al., "An enzyme-chromogenic surface plasmon resonance biosensor probe for hydrogen peroxide determination using a modified Trinder's reagent," Biosensors & Bioelectronics, 2008, pp. 455-460, vol. 24.
Virel, A., et al., "Modulated growth of nanoparticles. Application for sensing nerve gases," Analytical Chemistry, 2009, pp. 268-272, vol. 81.
Pollegioni, L., et al., "Cholesterol oxidase: biotechnological applications," The FEBS Journal, 2009, pp. 6857-6870, vol. 276.
Caseli, L., et al., "Immobilization of alcohol dehyrogenase in phospholipid Langmuir-Blodgett films to detect ethanol," Langmuir, 2009, pp. 3057-3061, vol. 25.
Lequin, Rudolf M., "Enzyme Immunoassay (EIA)/Enzyme-Linked Immunosorbent Assay (ELISA)," Clinical Chemistry, 2005, pp. 2415-2418, vol. 51.
Bates, D.L., "Enzyme amplification in diagnostics," Trends in Biotechnology, 1987, pp. 204-209, vol. 5.
Shlyahovsky, B., et al., "Biocatalytic evolution of a biocatalyst marker: towards the ultrasensitive detection of immunocomplexes and DNA analysis," Angewandte Chemie International Edition in English, 2006, pp. 4815-4819, vol. 45.
Khan, A.R., et al., "Molecular mechanisms for the conversion of zymogens to active proteolytic enzymes," Protein Science, 1998, pp. 815-836, vol. 7.
Wu, Jia-Wei, et al., "Kinetic analysis of a simplified scheme of autocatalytic zymogen activation," European Journal of Biochemistry, 2001, pp. 1547-1553, vol. 268.
Barrett, Dennis, "Zymogen Activation as a Sensitive Enzyme-Amplifying Assay for a Protease with Tryptic Specificity," The Biochemical Journal, 1970, pp. 57-59, vol. 117.

(Continued)

Primary Examiner — Maryam Monshipouri
(74) Attorney, Agent, or Firm — Tristan A. Fuierer; Moore & Van Allen, PLLC

(57) ABSTRACT

The present invention disclosed the cloning and the purification of a mutant of prethrombin-2, which contains a thrombin cleavage site instead of a factor Xa cleavage site. The stable mutant prethrombin-2 is able to convert itself autocatalytically into active α-thrombin in the absence of ecarin or factor Xa. The new concept of signal amplification using self-replicating enzymes can be applied to improve sensitivity of α-thrombin assays and also for the preparation of different enzymes.

14 Claims, 4 Drawing Sheets

(56) References Cited

PUBLICATIONS

Figure 1:
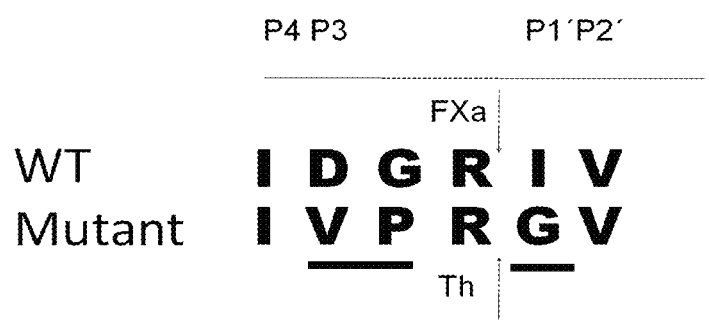

Weizmann, Y., et al., "Autonomous fueled mechanical replication of nucleic acid templates for the amplified optical detection of DNA," Angewandte Chemie International Edition in English, 2006, pp. 2238-2242, vol. 45.

Weizmann, Y., et al., "An autonomous fueled machine that replicates catalytic nucleic acid templates for the amplified optical analysis of DNA," Nature Protocols, 2006, pp. 554-558, vol. 1.

Leytus, Steven P., et al., "New class of sensitive and selective fluorogenic substrates for serine proteinases," The Biochemical Journal, 1983, pp. 253-260, vol. 215.

Ramjee, M.K., "The use of fluorogenic substrates to monitor thrombin generation for the analysis of plasma and whole blood coagulation," Analytical Biochemistry, 2000, pp. 11-18, vol. 277.

Chang, Jui-Yoa, "Thrombin specificity," European Journal of Biochemistry, 1985, pp. 217-224, vol. 151.

Soejima, K., et al., "An efficient refolding method for the preparation of recombinant human prethrombin-2 and characterization of the recombinant-derived alpha-thrombin," Journal of Biochemistry, 2001, pp. 269-277, vol. 130.

Saa, L., et al., "Analytical applications of enzymatic growth of quantum dots," Chemistry: A European Journal, 2010, pp. 6187-6192, vol. 16.

Rob, J.A., et al., "A rapid and highly sensitive chromogenic microplate assay for quantification of rat and human prothrombin," Analytical Biochemistry, 1997, pp. 222-225, vol. 245.

Virel, A., et al., "Quantification of prothrombin in human plasma amplified by autocatalytic reaction," Analytical Chemistry, 2012, pp. 2380-2387, vol. 84.

International Search Report dated Feb. 12, 2013.

SEQUENCE LISTING

<160> NUMBER OF SEQ ID NOS: 18

<210> SEQ ID NO 1
<211> LENGTH: 339
<212> TYPE: PRT
<213> ORGANISM: Mus musculus
<220> FEATURE:
<221> NAME/KEY: MISC_FEATURE
<222> LOCATION: (3)..(12)
<223> OTHER INFORMATION: Histidine tail
<220> FEATURE:
<221> NAME/KEY: MUTAGEN
<222> LOCATION: (79)..(80)
<223> OTHER INFORMATION: Mutated residues obtained by directed
      mutagenesis
<220> FEATURE:
<221> NAME/KEY: MUTAGEN
<222> LOCATION: (82)..(82)
<223> OTHER INFORMATION: Mutated residues obtained by directed
      mutagenesis

<400> SEQUENCE: 1

Met Gly His His His His His His His His Ser Ser Gly His
1               5                   10                  15

Ile Asp Ser Asp Ile Lys Thr Thr Glu Asn Leu Tyr Phe Gln Gly Ser
            20                  25                  30

Thr Thr Asp Ala Glu Phe His Thr Phe Phe Asn Glu Lys Thr Phe Gly
        35                  40                  45

Leu Gly Glu Ala Asp Cys Gly Leu Arg Pro Leu Phe Glu Lys Lys Ser
    50                  55                  60

Leu Lys Asp Thr Thr Glu Lys Glu Leu Leu Asp Ser Tyr Ile Val Pro
65                  70                  75                  80

Arg Gly Val Glu Gly Trp Asp Ala Glu Lys Gly Ile Ala Pro Trp Gln
                85                  90                  95

Val Met Leu Phe Arg Lys Ser Pro Gln Glu Leu Leu Cys Gly Ala Ser
            100                 105                 110

Leu Ile Ser Asp Arg Trp Val Leu Thr Ala Ala His Cys Ile Leu Tyr
        115                 120                 125

Pro Pro Trp Asp Lys Asn Phe Thr Glu Asn Asp Leu Leu Val Arg Ile
    130                 135                 140

Gly Lys His Ser Arg Thr Arg Tyr Glu Arg Asn Val Glu Lys Ile Ser
145                 150                 155                 160

Met Leu Glu Lys Ile Tyr Val His Pro Arg Tyr Asn Trp Arg Glu Asn
                165                 170                 175

Leu Asp Arg Asp Ile Ala Leu Leu Lys Leu Lys Lys Pro Val Pro Phe
            180                 185                 190

Ser Asp Tyr Ile His Pro Val Cys Leu Pro Asp Lys Gln Thr Val Thr
        195                 200                 205

Ser Leu Leu Arg Ala Gly Tyr Lys Gly Arg Val Thr Gly Trp Gly Asn
    210                 215                 220

Leu Arg Glu Thr Trp Thr Thr Asn Ile Asn Glu Ile Gln Pro Ser Val
225                 230                 235                 240

Leu Gln Val Val Asn Leu Pro Ile Val Glu Arg Pro Val Cys Lys Ala
                245                 250                 255

Ser Thr Arg Ile Arg Ile Thr Asp Asn Met Phe Cys Ala Gly Phe Lys
            260                 265                 270

Val Asn Asp Thr Lys Arg Gly Asp Ala Cys Glu Gly Asp Ser Gly Gly
        275                 280                 285

Pro Phe Val Met Lys Ser Pro Phe Asn Asn Arg Trp Tyr Gln Met Gly

```
                    290                 295                 300

Ile Val Ser Trp Gly Glu Gly Cys Asp Arg Lys Gly Lys Tyr Gly Phe
305                 310                 315                 320

Tyr Thr His Val Phe Arg Leu Lys Arg Trp Ile Gln Lys Val Ile Asp
                    325                 330                 335

Gln Phe Gly

<210> SEQ ID NO 2
<211> LENGTH: 322
<212> TYPE: PRT
<213> ORGANISM: Homo sapiens
<220> FEATURE:
<221> NAME/KEY: MISC_FEATURE
<222> LOCATION: (5)..(10)
<223> OTHER INFORMATION: Histidine tail
<220> FEATURE:
<221> NAME/KEY: MUTAGEN
<222> LOCATION: (61)..(62)
<223> OTHER INFORMATION: Mutated residues obtained by directed
      mutagenesis
<220> FEATURE:
<221> NAME/KEY: MUTAGEN
<222> LOCATION: (64)..(64)
<223> OTHER INFORMATION: Mutated residues obtained by directed
      mutagenesis

<400> SEQUENCE: 2

Met Arg Gly Ser His His His His His Gly Ser Val Asp Thr Ala
1               5                   10                  15

Thr Ser Glu Tyr Gln Thr Phe Phe Asn Pro Arg Thr Phe Gly Ser Gly
                20                  25                  30

Glu Ala Asp Cys Gly Leu Arg Pro Leu Phe Glu Lys Lys Ser Leu Glu
            35                  40                  45

Asp Lys Thr Glu Arg Glu Leu Leu Glu Ser Tyr Ile Val Pro Arg Gly
        50                  55                  60

Val Glu Gly Ser Asp Ala Glu Ile Gly Met Ser Pro Trp Gln Val Met
65                  70                  75                  80

Leu Phe Arg Lys Ser Pro Gln Glu Leu Leu Cys Gly Ala Ser Leu Ile
                85                  90                  95

Ser Asp Arg Trp Val Leu Thr Ala Ala His Cys Leu Leu Tyr Pro Pro
            100                 105                 110

Trp Asp Lys Asn Phe Thr Glu Asn Asp Leu Leu Val Arg Ile Gly Lys
        115                 120                 125

His Ser Arg Thr Arg Tyr Glu Arg Asn Ile Glu Lys Ile Ser Met Leu
130                 135                 140

Glu Lys Ile Tyr Ile His Pro Arg Tyr Asn Trp Arg Glu Asn Leu Asp
145                 150                 155                 160

Arg Asp Ile Ala Leu Met Lys Leu Lys Lys Pro Val Ala Phe Ser Asp
                165                 170                 175

Tyr Ile His Pro Val Cys Leu Pro Asp Arg Glu Thr Ala Ala Ser Leu
            180                 185                 190

Leu Gln Ala Gly Tyr Lys Gly Arg Val Thr Gly Trp Gly Asn Leu Lys
        195                 200                 205

Glu Thr Trp Thr Ala Asn Val Gly Lys Gly Gln Pro Ser Val Leu Gln
    210                 215                 220

Val Val Asn Leu Pro Ile Val Glu Arg Pro Val Cys Lys Asp Ser Thr
225                 230                 235                 240

Arg Ile Arg Ile Thr Asp Asn Met Phe Cys Ala Gly Tyr Lys Pro Asp
                245                 250                 255
```

-continued

```
Glu Gly Lys Arg Gly Asp Ala Cys Glu Gly Asp Ser Gly Gly Pro Phe
            260                 265                 270
Val Met Lys Ser Pro Phe Asn Arg Trp Tyr Gln Met Gly Ile Val
        275                 280                 285
Ser Trp Gly Glu Gly Cys Asp Arg Asp Gly Lys Tyr Gly Phe Tyr Thr
290                 295                 300
His Val Phe Arg Leu Lys Lys Trp Ile Gln Lys Val Ile Asp Gln Phe
305                 310                 315                 320
Gly Glu

<210> SEQ ID NO 3
<211> LENGTH: 339
<212> TYPE: PRT
<213> ORGANISM: Mus musculus
<220> FEATURE:
<221> NAME/KEY: MISC_FEATURE
<222> LOCATION: (3)..(10)
<223> OTHER INFORMATION: Histidine tail

<400> SEQUENCE: 3

Met Gly His His His His His His His His Ser Ser Gly His
1               5                   10                  15
Ile Asp Ser Asp Ile Lys Thr Thr Glu Asn Leu Tyr Phe Gln Gly Ser
            20                  25                  30
Thr Thr Asp Ala Glu Phe His Thr Phe Asn Glu Lys Thr Phe Gly
        35                  40                  45
Leu Gly Glu Ala Asp Cys Gly Leu Arg Pro Leu Phe Glu Lys Lys Ser
50                  55                  60
Leu Lys Asp Thr Thr Glu Lys Glu Leu Leu Asp Ser Tyr Ile Asp Gly
65                  70                  75                  80
Arg Ile Val Glu Gly Trp Asp Ala Glu Lys Gly Ile Ala Pro Trp Gln
            85                  90                  95
Val Met Leu Phe Arg Lys Ser Pro Gln Glu Leu Leu Cys Gly Ala Ser
        100                 105                 110
Leu Ile Ser Asp Arg Trp Val Leu Thr Ala Ala His Cys Ile Leu Tyr
    115                 120                 125
Pro Pro Trp Asp Lys Asn Phe Thr Glu Asn Asp Leu Leu Val Arg Ile
130                 135                 140
Gly Lys His Ser Arg Thr Arg Tyr Glu Arg Asn Val Glu Lys Ile Ser
145                 150                 155                 160
Met Leu Glu Lys Ile Tyr Val His Pro Arg Tyr Asn Trp Arg Glu Asn
                165                 170                 175
Leu Asp Arg Asp Ile Ala Leu Leu Lys Leu Lys Lys Pro Val Pro Phe
            180                 185                 190
Ser Asp Tyr Ile His Pro Val Cys Leu Pro Asp Lys Gln Thr Val Thr
        195                 200                 205
Ser Leu Leu Arg Ala Gly Tyr Lys Gly Arg Val Thr Gly Trp Gly Asn
    210                 215                 220
Leu Arg Glu Thr Trp Thr Thr Asn Ile Asn Glu Ile Gln Pro Ser Val
225                 230                 235                 240
Leu Gln Val Val Asn Leu Pro Ile Val Glu Arg Pro Val Cys Lys Ala
                245                 250                 255
Ser Thr Arg Ile Arg Ile Thr Asp Asn Met Phe Cys Ala Gly Phe Lys
            260                 265                 270
Val Asn Asp Thr Lys Arg Gly Asp Ala Cys Glu Gly Asp Ser Gly Gly
```

```
                275                 280                 285

Pro Phe Val Met Lys Ser Pro Phe Asn Asn Arg Trp Tyr Gln Met Gly
    290                 295                 300

Ile Val Ser Trp Gly Glu Gly Cys Asp Arg Lys Gly Lys Tyr Gly Phe
305                 310                 315                 320

Tyr Thr His Val Phe Arg Leu Lys Arg Trp Ile Gln Lys Val Ile Asp
                325                 330                 335

Gln Phe Gly

<210> SEQ ID NO 4
<211> LENGTH: 322
<212> TYPE: PRT
<213> ORGANISM: Homo sapiens
<220> FEATURE:
<221> NAME/KEY: MISC_FEATURE
<222> LOCATION: (5)..(10)
<223> OTHER INFORMATION: Histidine tail

<400> SEQUENCE: 4

Met Arg Gly Ser His His His His Gly Ser Val Asp Thr Ala
1               5                   10                  15

Thr Ser Glu Tyr Gln Thr Phe Phe Asn Pro Arg Thr Phe Gly Ser Gly
                20                  25                  30

Glu Ala Asp Cys Gly Leu Arg Pro Leu Phe Glu Lys Lys Ser Leu Glu
            35                  40                  45

Asp Lys Thr Glu Arg Glu Leu Leu Glu Ser Tyr Ile Asp Gly Arg Ile
        50                  55                  60

Val Glu Gly Ser Asp Ala Glu Ile Gly Met Ser Pro Trp Gln Val Met
65                  70                  75                  80

Leu Phe Arg Lys Ser Pro Gln Glu Leu Leu Cys Gly Ala Ser Leu Ile
                85                  90                  95

Ser Asp Arg Trp Val Leu Thr Ala Ala His Cys Leu Leu Tyr Pro Pro
                100                 105                 110

Trp Asp Lys Asn Phe Thr Glu Asn Asp Leu Leu Val Arg Ile Gly Lys
            115                 120                 125

His Ser Arg Thr Arg Tyr Glu Arg Asn Ile Glu Lys Ile Ser Met Leu
        130                 135                 140

Glu Lys Ile Tyr Ile His Pro Arg Tyr Asn Trp Arg Glu Asn Leu Asp
145                 150                 155                 160

Arg Asp Ile Ala Leu Met Lys Leu Lys Lys Pro Val Ala Phe Ser Asp
                165                 170                 175

Tyr Ile His Pro Val Cys Leu Pro Asp Arg Glu Thr Ala Ala Ser Leu
                180                 185                 190

Leu Gln Ala Gly Tyr Lys Gly Arg Val Thr Gly Trp Gly Asn Leu Lys
            195                 200                 205

Glu Thr Trp Thr Ala Asn Val Gly Lys Gly Gln Pro Ser Val Leu Gln
        210                 215                 220

Val Val Asn Leu Pro Ile Val Glu Arg Pro Val Cys Lys Asp Ser Thr
225                 230                 235                 240

Arg Ile Arg Ile Thr Asp Asn Met Phe Cys Ala Gly Tyr Lys Pro Asp
                245                 250                 255

Glu Gly Lys Arg Gly Asp Ala Cys Glu Gly Asp Ser Gly Gly Pro Phe
            260                 265                 270

Val Met Lys Ser Pro Phe Asn Asn Arg Trp Tyr Gln Met Gly Ile Val
        275                 280                 285
```

Ser Trp Gly Glu Gly Cys Asp Arg Asp Gly Lys Tyr Gly Phe Tyr Thr
    290                 295                 300

His Val Phe Arg Leu Lys Lys Trp Ile Gln Lys Val Ile Asp Gln Phe
305                 310                 315                 320

Gly Glu

<210> SEQ ID NO 5
<211> LENGTH: 924
<212> TYPE: DNA
<213> ORGANISM: Mus musculus
<220> FEATURE:
<221> NAME/KEY: mutation
<222> LOCATION: (140)..(140)
<223> OTHER INFORMATION: Mutated residues obtained by directed
      mutagenesis
<220> FEATURE:
<221> NAME/KEY: mutation
<222> LOCATION: (142)..(143)
<223> OTHER INFORMATION: Mutated residues obtained by directed
      mutagenesis
<220> FEATURE:
<221> NAME/KEY: mutation
<222> LOCATION: (148)..(149)
<223> OTHER INFORMATION: Mutated residues obtained by directed
      mutagenesis

<400> SEQUENCE: 5
accaccgatg cggagttcca caccttcttc aatgagaaga ccttcggcct tggggaggca      60
gactgtggcc tgcggccttt gttcgagaag aagtcgttga agacacaac cgaaaaggag     120 cttcttgact cttacatagt cccgcgcggc gtggagggct gggacgctga aagggtatc     180 gcccctggc aggtgatgct ttttcggaag agtccccaag agctgctgtg tggggccagc    240
cttatcagtg accgatgggt cctcactgct gcccactgca ttctgtaccc accctgggac    300
aagaacttca ctgagaatga cctcctggtg cgcattggca gcattcccg aaccagatat    360 gagcggaatg ttgaaaagat ctccatgctg gaaaagatct acgtccaccc cagatataac    420
tggcgggaga acctagaccg cgatatcgct ctgctcaagc taaagaaacc tgtaccctc    480 agtgactata ttcaccccgt gtgtttgcca gacaagcaga cagtaaccag cttgctccgg    540
gctggttata aagggcgggt gacaggctgg ggcaaccttc gggagacatg gacaaccaac    600
atcaatgaga tacagcccag cgtcctgcag gtggtgaacc tgcccattgt agagcggcca    660
gtgtgcaagg cctccacccg gattcgaatt actgacaaca tgttctgtgc tggcttcaag    720
gtgaatgaca ccaagcgagg agatgcttgt gaaggtgaca gtggaggacc ttttgtcatg    780
aagagcccct ttaacaaccg ctggtatcaa atgggtattg tctcatgggg tgaaggatgt    840
gaccggaagg ggaaatacgg cttctacacg catgtgttcc gtctgaaaag gtggatacag    900
aaagtcattg atcaatttgg atag                                           924

<210> SEQ ID NO 6
<211> LENGTH: 969
<212> TYPE: DNA
<213> ORGANISM: Homo sapiens
<220> FEATURE:
<221> NAME/KEY: mutation
<222> LOCATION: (182)..(182)
<223> OTHER INFORMATION: Mutated residues obtained by directed
      mutagenesis
<220> FEATURE:
<221> NAME/KEY: mutation
<222> LOCATION: (184)..(185)
<223> OTHER INFORMATION: Mutated residues obtained by directed
      mutagenesis
<220> FEATURE:

```
<221> NAME/KEY: mutation
<222> LOCATION: (190)..(191)
<223> OTHER INFORMATION: Mutated residues obtained by directed
      mutagenesis

<400> SEQUENCE: 6
atgagaggat cgcatcacca tcaccatcac ggatccgtcg acaccgccac cagtgagtac     60
cagactttct tcaatccgag gacctttggc tcgggagagg cagactgtgg gctgcgacct    120
ctgttcgaga agaagtcgct ggaggacaaa accgaaagag agctcctgga atcctacatc    180
gtcccgcgcg gtgtggaggg ctcggatgca gagatcggca tgtcaccttg gcaggtgatg    240
cttttccgga gagtcccca ggagctgctg tgtggggcca gcctcatcag tgaccgctgg    300
gtcctcaccg ccgcccactg cctcctgtac ccgccctggg acaagaactt caccgagaat    360
gaccttctgg tgcgcattgg caagcactcc cgcaccaggt acgagcgaaa cattgaaaag    420
atatccatgt tggaaaagat ctacatccac cccaggtaca actggcggga gaacctggac    480
cgggacattg ccctgatgaa gctgaagaag cctgttgcct tcagtgacta cattcaccct    540
gtgtgtctgc ccgacaggga cggcagcc agcttgctcc aggctggata caaggggcgg    600
gtgacaggct ggggcaacct gaaggagacg tggacagcca acgttggtaa ggggcagccc    660
agtgtcctgc aggtggtgaa cctgcccatt gtggagcggc cggtctgcaa ggactccacc    720
cggatccgca tcactgacaa catgttctgt gctggttaca gcctgatga agggaaacga    780 ggggatgcct gtgaaggtga cagtggggga ccctttgtca tgaagagccc ctttaacaac    840
cgctggtatc aaatgggcat cgtctcatgg ggtgaaggct gtgaccggga tgggaaatat    900
ggcttctaca cacatgtgtt ccgcctgaag aagtggatac agaaggtcat tgatcagttt    960
ggagagtag                                                            969

<210> SEQ ID NO 7
<211> LENGTH: 924
<212> TYPE: DNA
<213> ORGANISM: Mus musculus

<400> SEQUENCE: 7
accaccgatg cggagttcca caccttcttc aatgagaaga ccttcggcct tggggaggca     60
gactgtggcc tgcggccttt gttcgagaag aagtcgttga agacacaac cgaaaaggag    120 cttcttgact cttacataga cgggcgcatc gtggagggct gggacgctga aagggtatc    180 gcccccctggc aggtgatgct ttttcggaag agtccccaag agctgctgtg tggggccagc    240
cttatcagtg accgatgggt cctcactgct gcccactgca ttctgtaccc accctgggac    300
aagaacttca ctgagaatga cctcctggtg cgcattggca agcattcccg aaccagatat    360
gagcggaatg ttgaaaagat ctccatgctg gaaaagatct acgtccaccc cagatataac    420
tggcgggaga acctagaccg cgatatcgct ctgctcaagc taaagaaacc tgtacccttc    480
agtgactata ttcaccccgt gtgtttgcca gacaagcaga cagtaaccag cttgctccgg    540
gctggttata aagggcgggt gacaggctgg ggcaaccttc gggagacatg gacaaccaac    600
atcaatgaga tacagcccag cgtcctgcag gtggtgaacc tgcccattgt agagcggcca    660
gtgtgcaagg cctccacccg gattcgaatt actgacaaca tgttctgtgc tggcttcaag    720
gtgaatgaca ccaagcgagg agatgcttgt gaaggtgaca gtggaggacc ttttgtcatg    780 aagagccct ttaacaaccg ctggtatcaa atgggtattg tctcatgggg tgaaggatgt    840
gaccggaagg ggaaatacgg cttctacacg catgtgttcc gtctgaaaag gtggatacag    900
```
aaagtcattg atcaatttgg atag                                              924

<210> SEQ ID NO 8
<211> LENGTH: 969
<212> TYPE: DNA
<213> ORGANISM: Homo sapiens

<400> SEQUENCE: 8
atgagaggat cgcatcacca tcaccatcac ggatccgtcg acaccgccac cagtgagtac         60
cagactttct tcaatccgag gacctttggc tcgggagagg cagactgtgg gctgcgacct        120
ctgttcgaga agaagtcgct ggaggacaaa accgaaagag agctcctgga atcctacatc        180
gacgggcgca ttgtggaggg ctcggatgca gagatcggca tgtcaccttg gcaggtgatg        240
cttttccgga gagtcccca ggagctgctg tgtgggggcca gcctcatcag tgaccgctgg        300
gtcctcaccg ccgcccactg cctcctgtac ccgccctggg acaagaactt caccgagaat        360
gaccttctgg tgcgcattgg caagcactcc cgcaccaggt acgagcgaaa cattgaaaag        420
atatccatgt tggaaaagat ctacatccac cccaggtaca actggcggga gaacctggac        480
cgggacattg ccctgatgaa gctgaagaag cctgttgcct tcagtgacta cattcaccct        540
gtgtgtctgc ccgacaggga gacggcagcc agcttgctcc aggctggata caaggggcgg        600
gtgacaggct ggggcaacct gaaggagacg tggacagcca cgttggtaa ggggcagccc        660 agtgtcctgc agtggtgaa cctgcccatt gtggagcggc cggtctgcaa ggactccacc        720
cggatccgca tcactgacaa catgttctgt gctggttaca agcctgatga agggaaacga        780
ggggatgcct gtgaaggtga cagtggggga ccctttgtca tgaagagccc ctttaacaac        840
cgctggtatc aaatgggcat cgtctcatgg ggtgaaggct gtgaccggga tgggaaatat        900
ggcttctaca cacatgtgtt ccgcctgaag aagtggatac agaaggtcat tgatcagttt        960
ggagagtag                                                               969

<210> SEQ ID NO 9
<211> LENGTH: 28
<212> TYPE: DNA
<213> ORGANISM: Artificial Sequence
<220> FEATURE:
<223> OTHER INFORMATION: Synthetic Construct

<400> SEQUENCE: 9
cgcggatcca ccaccgatgc ggagttcc                                           28

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
ccgctcgagc tatccaaatt gatcaatgac                                         30

<210> SEQ ID NO 11
<211> LENGTH: 45
<212> TYPE: DNA
<213> ORGANISM: Artificial Sequence
<220> FEATURE:
<223> OTHER INFORMATION: Synthetic Construct

<400> SEQUENCE: 11
cttcttgact cttacatagt cccgcgcggc gtggagggct gggac                        45

<210> SEQ ID NO 12
<211> LENGTH: 45
<212> TYPE: DNA
<213> ORGANISM: Artificial Sequence
<220> FEATURE:
<223> OTHER INFORMATION: Synthetic Construct

<400> SEQUENCE: 12
gtcccagccc tccacgccgc gcgggactat gtaagagtca agaag         45

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
acgcgtcgac accgccacca gtgag         25

<210> SEQ ID NO 14
<211> LENGTH: 27
<212> TYPE: DNA
<213> ORGANISM: Artificial Sequence
<220> FEATURE:
<223> OTHER INFORMATION: Synthetic Construct

<400> SEQUENCE: 14
cccaagcttc tactctccaa actgatc         27

<210> SEQ ID NO 15
<211> LENGTH: 44
<212> TYPE: DNA
<213> ORGANISM: Artificial Sequence
<220> FEATURE:
<223> OTHER INFORMATION: Synthetic Construct

<400> SEQUENCE: 15
cctggaatcc tacatcgtcc cgcgcggtgt ggagggctcg gatg         44

<210> SEQ ID NO 16
<211> LENGTH: 44
<212> TYPE: DNA
<213> ORGANISM: Artificial Sequence
<220> FEATURE:
<223> OTHER INFORMATION: Synthetic Construct

<400> SEQUENCE: 16
catccgagcc ctccacaccg cgcgggacga tgtaggattc cagg         44

<210> SEQ ID NO 17
<211> LENGTH: 6
<212> TYPE: PRT
<213> ORGANISM: Homo sapiens

<400> SEQUENCE: 17

Ile Asp Gly Arg Ile Val
1               5

-continued

```
<210> SEQ ID NO 18
<211> LENGTH: 6
<212> TYPE: PRT
<213> ORGANISM: Homo sapiens

<400> SEQUENCE: 18

Ile Val Pro Arg Gly Val
1               5
```

METHOD FOR THE PRODUCTION OF HUMAN THROMBIN AND USES THEREOF

CROSS-REFERENCE TO RELATED APPLICATIONS

This application is filed under the provisions of 35 U.S.C. §371 and claims the priority of International Patent Application No. PCT/EP2012/071572 filed on 31 Oct. 2012 entitled "METHOD FOR THE PRODUCTION OF HUMAN THROMBIN AND USES THEREOF" in the name of Valery PAVLOV, et al, which claims priority to U.S. Provisional Patent Application No. 61/555,763 filed on Nov. 4, 2011 both of which are hereby incorporated by reference herein in their entirety.

FIELD OF THE INVENTION

The invention refers to the field of biotechnology. Specifically, the invention relates to a stable recombinant mutated prethrombin-2 which is able to convert itself auto-catalytically into active α-thrombin that can be used as a haemostatic. Another aspect of the invention includes the application of mutated recombinant prethrombin-2 and the α-thrombin obtained by itself-autocatalytic activity, in diagnostics and/or prognostics of coagulation related-diseases.

BACKGROUND OF THE INVENTION

α-Thrombin plays an important role in hemostasis and hence is a highly useful protein for use as a hemostatic. Currently, α-thrombin is utilized in more than 1 000 000 patients in the USA each year [1]. The main source of α-thrombin is pooled human plasma collected from donors. The plasma is treated by complicated filtration and separation, however, no procedure is completely effective against viral particles derived from human blood [2].

Alternatively, recombinant α-thrombin can be produced that is devoid of the risks of viral particles. Thrombin is synthesized in the form of prothrombin which is one of proteolytic enzymes which are normally synthesized in their inactive form, known as proenzymes or zymogens, which can be cleaved by factor Xa or by ecarin, a protease found in snake poison, [3] at two places, Arg-Thr and Arg-Ile bonds. Cleavage at the first factor Xa site results in prethrombin-2, an inactive single-chain precursor that has the same size as α-thrombin. Activation of prethrombin-2 to α-thrombin occurs through internal rearrangement of the initial peptide chain upon cleavage of Arg-Ile bond with factor Xa or by ecarin [4]. The cleaved shorter peptide section does not leave the α-thrombin macromolecule but stays linked with the longer peptide sequence via an S—S bond.

Currently, it is impossible to directly express active recombinant α-thrombin from the gene fragment corresponding to prothrombin because the resulting protein will be always inactive prethrombin-2. The preparation of recombinant prethrombin-2 and its activation to α-thrombin by ecarin, has been described in the literature [5]. The main drawback of this procedure is the necessity to employ extremely dangerous ecarin, the primary reagent in the venom of the snake *Echis carinatus* [6] to activate α-thrombin. The removal of ecarin, significantly diminishes the yield and increases costs of α-thrombin preparation. Still there is no 100% assurance that recombinant α-thrombin is not contaminated with ecarin. Factor Xa can be used instead of lethal ecarin but it requires for its optimal operation a complex with factor V, platelet phospholipids and calcium [7], that also must be separated from α-thrombin.

On the other hand, enzymes, such us, α-thrombin, have been commonly used in different bioanalytical assays for detection and amplification of signal. They are employed in quantification of glucose [8], $H_2O_2$ [9], pesticides [10], cholesterol [11], and ethanol [12], and are the basis for ELISAs (enzyme linked immunosorbent assays) [13]. Enzyme amplification techniques [14] have been used to improve the sensitivity of several bioanalytical assays. In this sense, the state of the art discloses an assay including a double amplification cascade in which ecarin, converted prothrombin to α-thrombin to digest an artificial fluorogenic substrate [15]. As mentioned above, prothrombin is one of proteolytic enzymes which are normally synthesized in their inactive form, known as proenzymes or zymogens [16]. When the product of the proenzyme cleavage reaction catalyzes the same reaction, the process is called an autocatalytic activation [17]. Some examples of natural autocatalytic enzymes are trypsinogen, pepsinogen, or the blood coagulation factor XII [18]. The autocatalytic behavior of these enzymes could be applied for analytical purposes. Moreover, tests for α-thrombin activity are used to evaluate the rate of blood coagulation, therefore it is important to develop sensitive methods to monitor its activity.

The signal obtained by a low concentration of an enzyme can be considerably amplified by means of an autocatalytic reaction. The use of zymogens in bioanalysis is limited since all known natural autocatalytic proenzymes are unstable in vitro and their preparations always contain traces of corresponding active enzymes [19]. To the best of our knowledge, there are still no commercially available kits based on natural autocatalytic proenzymes. Previously, the inventors used the self-replicating DNA machines based on endonucleases to create signal amplification networks [20, 21]. Unfortunately, DNA machines are not stable in body liquids and can not be applied for the analysis of blood derived samples.

In spite of considerable research into the signal amplification in bioassays, specifically, using self-replicating enzymes and also the preparation and production of these enzymes, more studies are still needed. Moreover, it has not yet been found a proenzyme stable in vitro without traces of corresponding active enzymes and also with autocatalytic activity, particularly these is not disclosures in the prior art about a recombinant prethrombin-2, with autocatalytic features, which show stability in vitro, without traces of α-thrombin.

DESCRIPTION OF THE INVENTION

Brief Description of the Invention

The present invention, overcomes these problems in the art by disclosing a new methodology for production of a mouse (SEQ ID NO: 1) and human (SEQ ID NO: 2) mutant recombinant stable prethrombin-2 which are able to convert itself auto-catalytically into active α-thrombin in the absence of ecarin or factor Xa or any other substance.

The method for obtaining a stable mutant recombinant prethrombin-2 consists of changing the cleavage site of a recombinant proenzyme by site directed mutagenesis to obtain a stable protein that can be cleaved by the corresponding active enzyme. Specifically, the inventors have modified the cleavage site of native or wild type (WT) mouse (SEQ ID NO: 3) and human (SEQ ID NO: 4) prethrombin-2 to a α-thrombin cleavage site to obtain a stable artificial autocatalytic enzyme. The mutant recombinant proenzyme is activated by α-thrombin triggering the autocatalytic reaction. The concept of signal amplification using self-replicating enzymes can be applied to improve sensitivity of α-thrombin assays and also for the preparation of different enzymes. Therefore, the present invention displays an autocatalytic mutant recombinant enzyme, prethrombin-2, and its application for the signal amplification in bioassays for the detection of α-thrombin/prothrombin and for the synthesis of recombinant α-thrombin.

Surprisingly, the mutated prethrombin-2 disclosed in the present invention is completely stable, without any trace of thrombin, or any other proteases or any undesired factor, component, contaminant, etc, which may initiate an undesired and/or uncontrolled cleavage of the mutant prethrombin-2. The invention described herein, allows total control of the autocatalysis of prethrombin-2 due to the unexpected stability shown by the mutated prethrombin-2 of the invention. This stability feature of mutated prethrombin-2 of present invention has as advantage its use in in vitro assays for detection of α-thrombin/prothrombin, with more accuracy as far as the stable mutated prethrombin-2 of the invention has not autocatalytic basal activity due to contaminant, as the ones previously mentioned, and its autocatalysis is only triggered by the amount of α-thrombin present in the assay sample.

Thus, in a first aspect the present invention refers to a stable and autocatalytic mutant prethrombin-2, from murine or human origins (SEQ ID NO: 1 or SEQ ID NO: 2, respectively) and their corresponding DNA encoding sequences (SEQ ID NO: 5 or SEQ ID NO: 6, respectively).

In a second aspect, the invention refers to the use of at least one of the mutated prethrombin-2 proenzymes or their nucleotide encoding sequences as mentioned above for the synthesis of α-thrombin.

In a third aspect, the present invention refers to the use of at least one of the mutated prethrombin-2 proenzymes for the manufacture of a kit for the in vitro diagnosis and/or prognosis of coagulation-related diseases.

In another aspect, the present invention refers to the use of at least one of the mutated prethrombin-2 proenzymes for the manufacture of a kit for detection of α-thrombin/prothrombin.

In another aspect, the invention refers to a kit which comprises at least one of the mutated prethrombin-2 proenzymes disclosed in the present invention. The kit disclosed herein also could include other reagents, i.e.: assay reagents, buffers and sterile saline or another pharmaceutically acceptable emulsion and suspension base. In addition, the kits may include instructional materials containing directions (e.g., protocols) for the practice of the assay methods of this invention.

In another aspect, the present invention refers to the use of the kit disclosed herein for the in vitro diagnosis and/or prognosis of coagulation-related diseases. The coagulation-related disease is selected from the group comprising: haemophilia, thrombosis, inherited prothrombin deficiency Type I or Type II, acquired prothrombin deficiency and von Willebrand disease.

In another aspect, the present invention refers to a method for preparing active α-thrombin using the mutant recombinant prethrombin-2 disclosed in the present invention.

In still another aspect, the invention refers to an in vitro method of diagnosis and/or prognosis of coagulation-related diseases which comprises determining in a sample from a subject, the expression or activity level of α-thrombin/prothrombin using the kit disclosed herein and the comparison of said expression level with respect to the expression values obtained from healthy controls. The α-thrombin/prothrombin expression or activity levels are analyzed in a sample of blood. For this purpose is extremely important that the prethrombin-2 to be used in the amplification reaction wherein the in vitro assay is based was stable, because traces of thrombin or any other proteases contaminating the prethrombin-2 to be used in thrombin detection in biological samples would render artefacts.

Unless defined otherwise, all technical and scientific terms used herein have the same meaning as commonly understood by one of ordinary skill in the art to which this invention belongs. However, for ease of reference, some of these terms will now be defined.

The expression or activity level of a disease-associated α-thrombin/prothrombin is information in a number of ways. For example, a differential expression of a disease-associated α-thrombin/prothrombin compared to a control may be used as a diagnostic that a patient suffers from the disease. Expression or activity levels of a disease-associated α-thrombin/prothrombin may also be used to monitor the treatment and disease state of a patient. Furthermore, expression or activity levels of the disease-associated α-thrombin/prothrombin may allow the screening of drug candidates for altering a particular expression profile or suppressing an expression profile associated with the disease. In the present invention, the terms "expression or activity" in relation with α-thrombin/prothrombin levels are used interchangeably.

The term "sample" refers preferably to a sample of a fluid such as a solution and more preferably refers to a sample of a body fluid. Samples of body fluids can be obtained by well known techniques and include, preferably, samples of blood, plasma, serum, more preferably, samples of plasma.

The term "subject" as used herein refers to an animal, preferably a mammal, most preferably a human being, including both young and old human beings of both sexes which may suffer from or are predisposed to a pathology. The subject according to this aspect of the present invention may suffer from a pathology associated with abnormal expression or activity of coagulation pathway. The terms "subject" and "patient" could be used interchangeably throughout the present invention.

The term "stable prethrombin-2" means, within present invention, a prethrombin-2 in a sample free of thrombin or any other proteases or any undesired factor, component, contaminant, etc, which may trigger autocatalytic activity of prethrombin-2 itself.

FIGURE LEGENDS

FIG. 1. Sequence alignment of the cleavage site of wild type (WT) and mutant prethrombin-2. FXa cleavage site present in WT prethrombin-2, corresponding to residues IDGRIV, was changed to IVPRGV which corresponds to a α-thrombin (Th) cleavage site. Changed amino acids are underlined.

Figure 2:
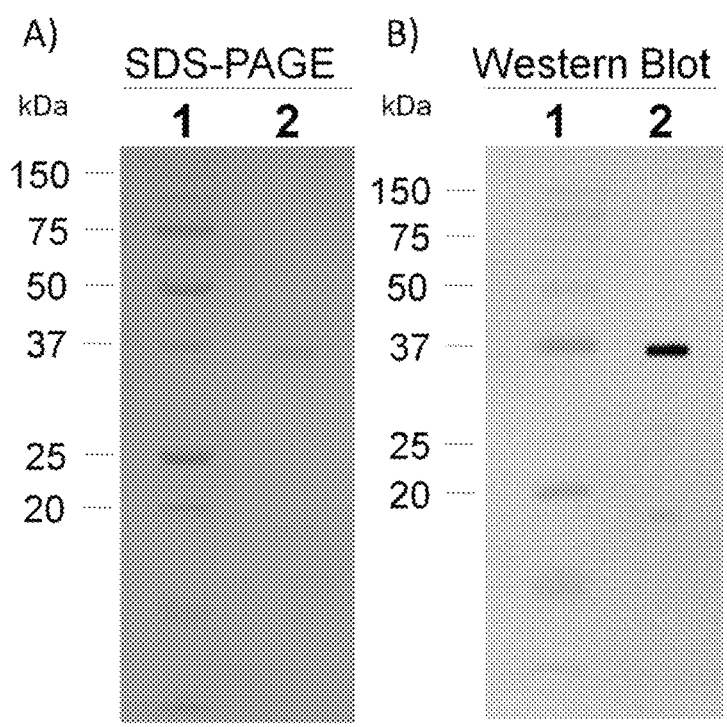

FIG. 2. Analysis of the purified mouse mutant prethrombin-2. A) 12% SDS-PAGE stained with Coomassie Brilliant Blue. B) Nitrocellulose membrane probed with anti-His-tag mouse monoclonal antibodies. Lane 1, molecular mass references; lane 2, 0.3 µg mutant prethrombin-2.

Figure 3:
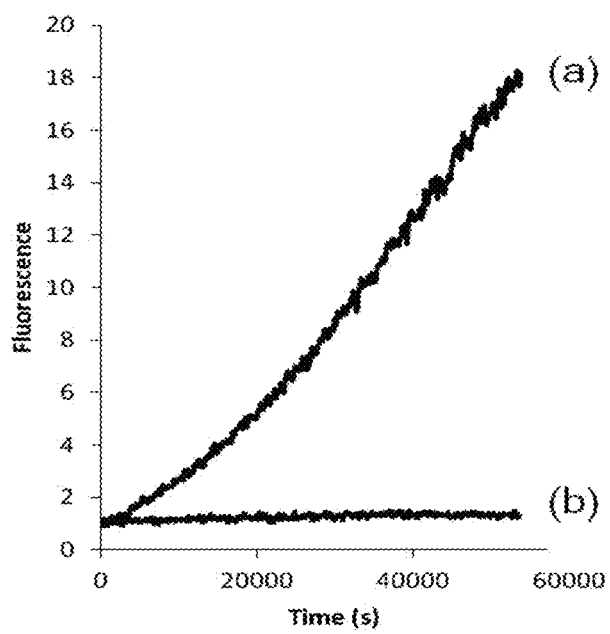

FIG. 3. Stability assay of human mutant prethrombin-2. Evolution of fluorescence intensity in samples containing human wild type recombinant prethrombin-2 ($1.6 \times 10^{-6}$ M) (a) or human mutant recombinant prethrombin-2 ($1.6 \times 10^{-6}$ M) (b), with the fluorogenic substrate rhodamine 110, bis-(p-tosyl-L-glycyl-L-prolyl-L-arginine amide) ($4 \times 10^{-6}$ M) (Invitrogen) in 50 mM Tris-HCl, pH 9.0, 150 mM NaCl.

Figure 4:
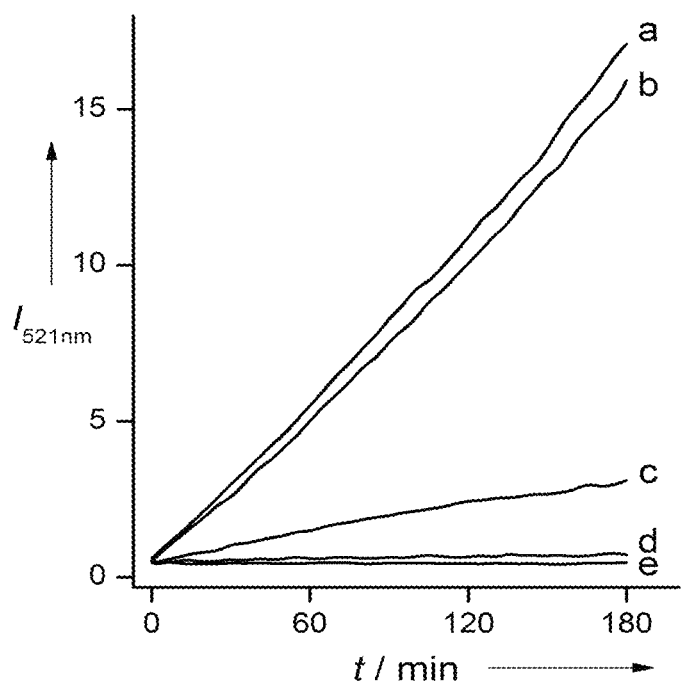

FIG. 4. Evolution of fluorescence intensity in samples containing a) $2.2 \times 10^{-12}$ M human wild type α-thrombin and $2.1 \times 10^{-7}$ M human mutant prethrombin-2; b) $2.2 \times 10^{-12}$ M human wild type α-thrombin and $2.1 \times 10^{-7}$ M mouse mutant prethrombin-2; c) $2.2 \times 10^{-12}$ M human wild type α-thrombin; d) $2.1 \times 10^{-7}$ M human mutant prethrombin-2; e) $2.1 \times 10^{-7}$ M mouse mutant prethrombin-2.

Figure 5:
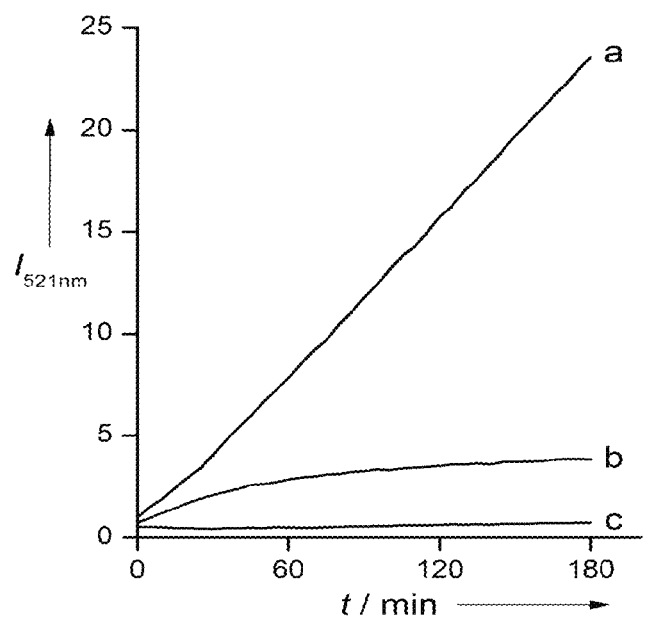

FIG. 5. Time courses of mutant prethrombin-2 activation and self-replication. a) $5.38 \times 10^{-9}$ M cleaved mutant prethrombin-2 and $2.3 \times 10^{-7}$ M untreated mutant prethrombin-2; b) $5.38 \times 10^{-9}$ M cleaved mutant prethrombin-2; c) $2.3 \times 10^{-7}$ M untreated mutant prethrombin-2.

Figure 6:
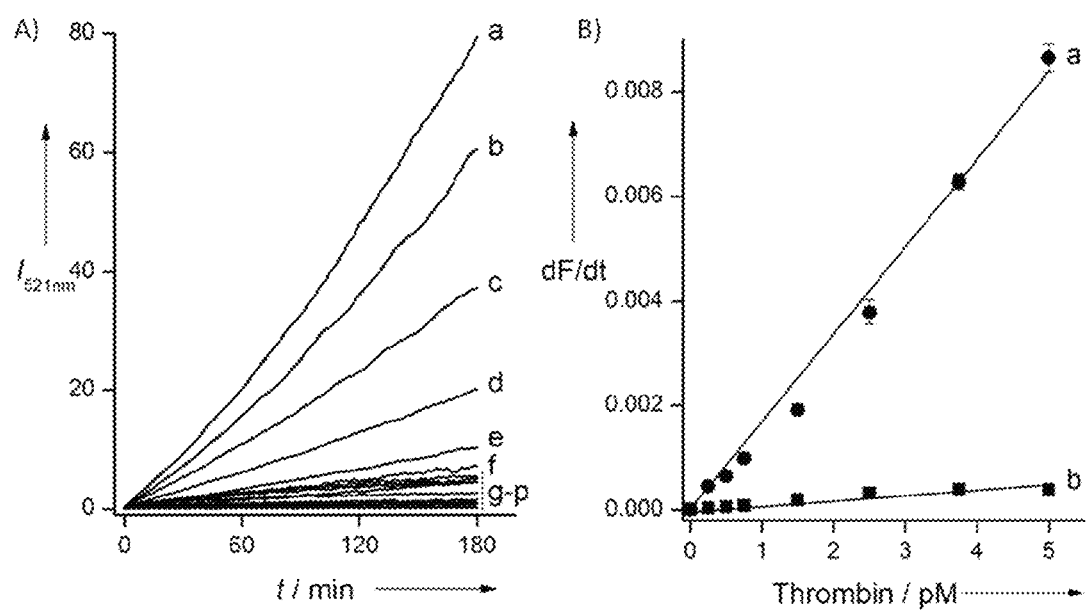

FIG. 6. A) Evolution of fluorescence intensity in the presence (curves a-h) of $5.3 \times 10^{-7}$ M mutant prethrombin-2 or its absence (curves i-p). The samples contained different concentrations of human α-thrombin: a) and i) $5 \times 10^{-12}$ M; b) and j) $3.75 \times 10^{-12}$ M; c) and k) $2.5 \times 10^{-12}$ M; d) and l) $1.5 \times 10^{-12}$ M; e) and m) $7.5 \times 10^{-13}$ M; f) and n) $5 \times 10^{-13}$ M; g) and o) $2.5 \times 10^{-13}$ M; h) and p) 0 M. B) Calibration curve of α-thrombin in the presence (curve a) and absence (curve b) of mutant prethrombin-2.

Figure 7:
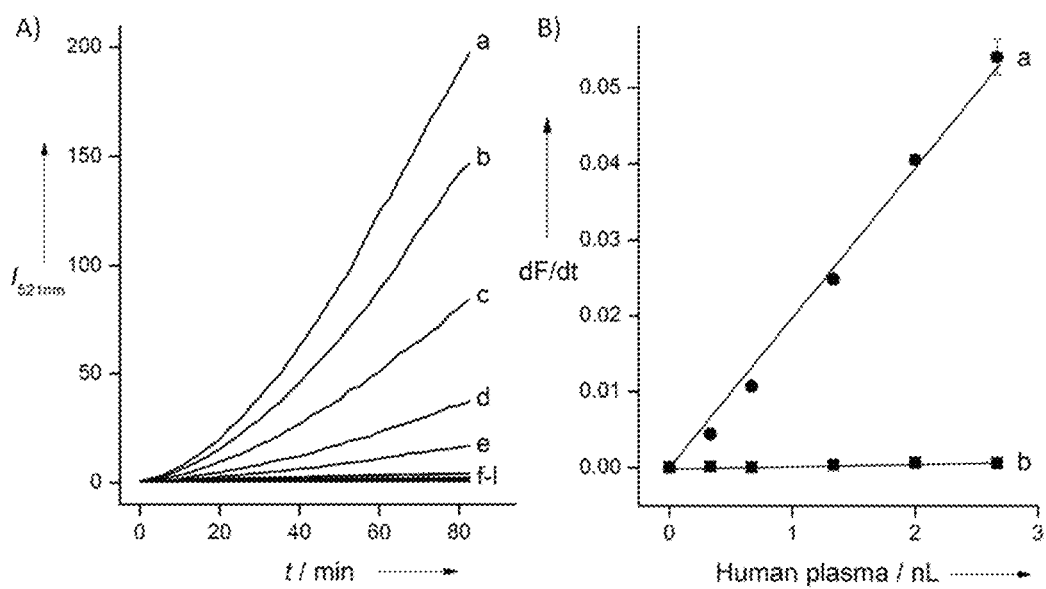

FIG. 7. A) Evolution of fluorescence intensity in human plasma samples in the presence of $1.5 \times 10^{-6}$ M mutant prethrombin-2 (curves a-f) or its absence (curves g-l). The samples contained $6 \times 10^{-8}$ M ecarin and different volumes of human plasma: a) and g) 2.6 nL; b) and h) 2 nL; c) and i) 1.3 nL; d) and j) 0.67 nL; e) and k) 0.33 nL; f) and l) 0 nL. B) Calibration curve of human plasma in the presence (curve a) or absence (curve b) of mutant prethrombin-2.

DETAILED DESCRIPTION OF THE INVENTION

Present invention relates to a mutant prethrombin-2 characterized by having SEQ ID NO: 1 or SEQ ID NO: 2 or their nucleotide encoding sequences characterized by SEQ ID NO: 5 or SEQ ID NO: 6, respectively.

In a particular embodiment of the invention, the mutant prethrombin-2 is SEQ ID NO: 2 or their nucleotide encoding sequence characterized by SEQ ID NO: 6.

In another particular embodiment of the invention, the mutant prethrombin-2 characterized by having SEQ ID NO: 2 or by their nucleotide encoding sequence: SEQ ID NO: 6 which is from human origin.

In another particular embodiment of the invention, the mutant prethrombin-2 disclosed in the present invention is characterized by having autocatalytic activity and by being stable in vitro.

Present invention also relates to the mutated prethrombin-2 mentioned above for use in the synthesis of α-thrombin or in the in vitro detection of α-thrombin/prothrombin in biological samples.

Present invention also discloses the use of the mutated prethrombin-2 mentioned above for the manufacture of a kit for the in vitro diagnosis and/or prognosis of coagulation-related diseases.

In a particular embodiment of the kit of the present invention, the coagulation-related disease is selected from the group comprising: haemophilia, thrombosis, inherited prothrombin deficiency Type I or Type II, acquired prothrombin deficiency and von Willebrand disease.

Present invention also discloses a mutant prethrombin-2 mentioned above for use in the in vitro diagnosis and/or prognosis of coagulation-related diseases. In a particular embodiment, the coagulation-related disease is selected from the group comprising: haemophilia, thrombosis, inherited prothrombin deficiency Type I or Type II, acquired prothrombin deficiency and von Willebrand disease.

Present invention also relates to a method for preparing α-thrombin which comprises the following steps:
1. Modify, preferably by site-direct mutagenesis, the DNA sequence encoding for the factor Xa cleavage site in wild type prethrombin-2 gene to the DNA sequence encoding for the α-thrombin cleavage site.
2. Insert the mutated DNA prethrombin-2 into an expression vector.
3. Transform a host cell with the vector disclosed in previous step.
4. Culturing the transformed host cell of previous step in an appropriate culture medium.
5. Harvest transformed host cells and solubilize proteins in inclusion bodies.
6. Isolating the supernatant to obtain purified mutant prethrombin-2.
7. Contacting the purified mutant prethrombin-2 obtained in previous step with α-thrombin.
8. Purifying the α-thrombin obtained in previous step 6.

In a preferred embodiment of the invention, the method disclosed herein it is characterized in that the amino acid sequence of factor Xa cleave site in wild type prethrombin-2 is SEQ ID NO: 17.

In a preferred embodiment of the invention, the method disclosed herein it is characterized in that the amino acid sequence of the thrombin cleave site in mutant prethrombin-2 is SEQ ID NO: 18.

In a preferred embodiment of the invention, the method disclosed herein it is characterized in that the ADN sequence of the wild type prethrombin-2 is selected from the group comprising SEQ ID NO: 5 or SEQ ID NO: 6.

In a preferred embodiment of the invention, the method disclosed herein it is characterized in that the vector is preferably a plasmid. Any vector or plasmid known in the prior art for the same purpose could be used. In this sense, any vector suitable for expression in bacteria containing T7 promoter and coding a N-terminal His tag may be employed. On the other hand, any vector suitable for expression in yeast, containing galactose or methanol inducible promoters and coding a His tag may also be used in present invention. More particularly the plasmid is pET-TEV-prethr-2 plasmid or pQE9-hprethr-2 plasmid.

In a preferred embodiment of the invention, the method disclosed herein it is characterized in that the host cell is selected from the group comprising: bacterial cells, animal cells and/or yeast.

In a more preferred embodiment of the invention the bacterial host cell is *E. coli*, preferably, *E. coli* XL1-blue, or *E. coli* BL21 or any strain derived thereof.

In a more preferred embodiment of the invention the host cell is a yeast selected from the group comprising: *Saccharomyces* sp. or *Pichia pastoris* or any strain derived thereof.

In a preferred embodiment of the invention, the method disclosed herein it is characterized in that the ratio prethrombin-2: α-thrombin of step 7 ranged $1:10^{-6}$.

In a preferred embodiment of the invention, the method disclosed herein it is characterized in that the purification of α-thrombin comprises at least one step of techniques of affinity chromatography.

Present invention also discloses a kit for detecting α-thrombin/prothrombin in a sample comprising the mutant prethrombin-2, murine or human as disclosed herein.

Present invention also discloses the use of the kit mentioned above for the in vitro diagnosis and/or prognosis of coagulation-related diseases.

In a preferred embodiment, the coagulation-related disease is selected from the group comprising: haemophilia, thrombosis, inherited prothrombin deficiency Type I or Type II, acquired prothrombin deficiency and von Willebrand disease.

Present invention also disclosed an in vitro method of diagnosis and/or prognosis of coagulation-related diseases which comprises the determination in a sample from a subject of the expression or activity level of α-thrombin/prothrombin using the kit mentioned above and the comparison of said expression or activity level with respect to the values for the same expression or activity obtained from healthy controls.

In a preferred embodiment of the in vitro method, the coagulation-related disease is selected from the group comprising: haemophilia, thrombosis, inherited prothrombin deficiency: Type I or Type II, acquired prothrombin deficiency and von Willebrand disease.

In a preferred embodiment of the in vitro method, the sample of the subject is selected from blood, plasma and/or serum, more preferably, samples of plasma.

Although any methods and materials similar or equivalent to those described herein can also be used in the practice or testing of the present invention, the preferred methods and materials are now described. It will be appreciated by those of skill in the art that, in light of the present disclosure, numerous modifications and changes can be made in the particular embodiments exemplified without departing from the intended scope of the invention.

The following examples illustrate the invention and should not be considered in a limiting sense, but rather in an illustrative sense of the invention.

Example 1

Cloning and Site Specific Mutations of Prethrombin-2 Gene

The present invention discloses the change the cleavage site of a recombinant proenzyme, prethrombin-2, by site directed mutagenesis to obtain a stable artificial autocatalytic enzyme. To achieve this purpose, the inventors have cloned the WT gene of prethrombin-2 and modified the factor Xa cleavage site in it to a thrombin cleavage site to obtain a stable artificial autocatalytic enzyme. The mutation strategy relies on converting the factor Xa cleavage site (Arg-Ile bond) into the α-Thrombin cleavage site by directed mutagenesis to create a self-replicative protease.

Briefly, for this approach, the sequences corresponding to human and mouse prethrombin-2 genes were cloned and five single mutations were introduced by, as mentioned above, site-directed mutagenesis in order to create a mutant prethrombin-2.

First, the vector pCMV-SPORT6 containing the full length mouse prothrombin cDNA was obtained from Geneservice (UK). The prethrombin-2 fragment was amplified from the same vector by PCR using PfuTurbo (Stratagene) and PCR nucleotide mix (Promega). Amplification primers were SEQ ID NO: 9 and SEQ ID NO: 10 containing BamHI and XhoI restriction sites respectively. The PCR product was run on an agarose gel, purified with QIAquick gel extraction kit (Qiagen) and digested with BamHI and XhoI (Takara). Afterwards, the fragment was purified using the QIAquick PCR purification kit (Qiagen) and ligated into the pET-TEV expression vector, a pET-19b vector modified by introducing a TEV protease cleavage site (generously provided by Dr. Lars Backman) giving pET-TEV-prethr-2 plasmid. The correctness of the inserted sequence was verified (MWG Germany). pET-TEV-prethr-2 plasmid was used as a template to mutate the prethrombin-2 gene. Site-direct specific mutations were introduced using the following primers: SEQ ID NO: 11 and SEQ ID NO: 12 with QuikChange II Site-Directed Mutagenesis Kit (Stratagene). The correctness of the mutant sequence was verified (MWG Germany).

The vector pOTB7 containing the full length human prothrombin cDNA was obtained from Geneservice (UK). The prethrombin-2 fragment was amplified from the same vector by PCR using PfuTurbo (Stratagene) and PCR nucleotide mix (Promega). Amplification primers were SEQ ID NO: 13 and SEQ ID NO: 14 containing SalI and HindIII restriction sites respectively. The PCR product was run on an agarose gel, purified with QIAquick gel extraction kit (Qiagen) and digested with SalI and HindIII (Takara). Afterwards, the fragment was purified using the QIAquick PCR purification kit (Qiagen) and ligated into the pQE9 expression vector (Qiagen), giving pQE9-hprethr-2 plasmid. The correctness of the inserted sequence was verified (MWG Germany). pQE9-hprethr-2 plasmid was used as a template to mutate the human prethrombin-2 gene. Site-direct specific mutations were introduced using the following primers SEQ ID NO: 15 and SEQ ID NO: 16 with QuikChange II Site-Directed Mutagenesis Kit (Stratagene). The correctness of the mutant sequence was verified (MWG Germany).

As a result, the, the FXa cleavage site present in wild type (WT) prethrombin-2, corresponding to residues with SEQ ID NO: 17 was changed to residues with SEQ ID NO: 18 which corresponds to the thrombin cleavage site. FIG. 1 shows the alignment of the FXa and thrombin cleavage sites of mutant prethrombin-2 and WT respectively. Changed amino acids are underlined. Thrombin selectively cleaves Arg-Gly bonds in fibrinogen and other polypeptides. Studies on the thrombin cleavage site from 30 different polypeptides revealed that the optimum cleavage site has the structure of P4-P3-Pro-Arg-P1'-P2' where P4 and P3 are hydrophobic amino acids and P1' and P2' are non acidic amino acids. It was also observed that polypeptides which contained Gly at P1' were especially susceptible to thrombin cleavage [24].

Example 2

Expression and Purification of Mutant Prethrombin-2

The plasmid contained the mutated sequences of human and mouse prethrombin-2 were used to transform *Escherichia coli* cells and the human and mouse mutant prothrombin-2 proteins were expressed and purified.

Particularly, *Escherichia coli* BL21 (DE3) cells were transformed by heat shock with the plasmid containing the mutant mouse prethrombin-2 gene. Cells were grown at 37° C. in Luria-Bertani media supplemented with 100 μg/ml ampicillin to reach an OD600≈0.7. Protein expression was induced by adding 0.1 mM isopropyl thio-β-D-galactoside. Cells were grown for 4 h at 37° C. and harvested by centrifugation. Protein purification from inclusion bodies was performed as described in Soejima et al. [25] with some modifications. After protein refolding, the sample was dialyzed against 50 mM Tris-HCl, pH 7.6, 150 mM NaCl, during two days at 4° C. without stirring. The dialyzed sample was centrifuged and the resulting supernatant was filtered. The pass-through fraction was loaded on a nickel HisTrap™ HP affinity column (GE Healthcare) controlled by an ÄKTA purifier equipment (GE Healthcare). Protein was eluted with a linear gradient from 0 to 500 mM of imidazole in 50 mM Tris-HCl, pH 7.6, 150 mM NaCl. Protein purity was investigated by 12% SDS-PAGE.

Electrophoretic analysis of the purified protein showed a single band corresponding to the expected size (FIG. 2A).

Protein identity was confirmed by Western blot using antibodies against His-tagged polypeptides (FIG. 2B).

For the purification of the human mutated prethrombin-2, E. coli XL1-blue cells were transformed by heat shock with the plasmid containing the mutant human prethrombin-2 gene. Cells were grown at 37° C. in Luria-Bertani media supplemented with 100 μg/ml ampicillin to reach an OD600≈0.6. Protein expression was induced by adding 1 mM isopropyl thio-β-D-galactoside. Cells were grown for 3 h at 37° C. and harvested by centrifugation. Protein purification from inclusion bodies was performed as described before for the mouse mutant prethrombin-2. After protein refolding, the sample was dialyzed against 50 mM Tris-HCl, pH 7.0, at 4° C. without stirring. The dialyzed sample was centrifuged and the resulting supernatant was filtered. The pass-through fraction was loaded on a HiTrap™ HeparinHP affinity column (GE Healthcare) controlled by an ÄKTA purifier equipment (GE Healthcare). Protein was eluted with a linear gradient from 0 to 2 M NaCl in 50 mM Tris-HCl, pH 7.0. Protein purity was also investigated by 12% SDS-PAGE (FIG. 2A).

Western Blot

Proteins, mouse mutant prethrombin-2 and human mutant prethrombin-2, were separated by 12% SDS-PAGE and electroblotted onto a nitrocellulose membrane. The membrane was then incubated for 1 h in phosphate-buffered saline (PBS), containing 0.05% Tween 20, and 10% defatted milk. Afterwards, the membrane was washed with PBS containing 0.05% Tween 20 and incubated with anti-His mouse monoclonal antibodies (GE Healthcare) for 1 h. Then, the membrane was washed with PBS containing 0.05% Tween 20 and further incubated with secondary rabbit antibodies antimouse IgG conjugated to alkaline phosphatase (Sigma-Aldrich) for 1 h. After washing with PBS containing 0.05% Tween 20, protein bands were developed with 5-bromo-4-chloro-3-indolyl phosphate/nitro blue tetrazolium solution (Fluka) (FIG. 2B).

Example 3

Stability Assay of Mutant Prethrombin-2

Stability assays were performed by mixing human WT or human mutant prethrombin-2 ($1.6 \times 10^{-6}$ M) both produced by recombination in E. coli, with the fluorogenic substrate rhodamine 110, bis-(p-tosyl-L-glycyl-L-prolyl-L-arginine amide) ($4 \times 10^{-6}$ M) (Invitrogen) in 50 mM Tris-HCl, pH 9.0, 150 mM NaCl. The fluorescence of the resulting solutions was monitored using λexcitation=498 nm and λemission=521 nm.

Stability assay measures in real time the enzymatic activity of active α-thrombin in the presence of the fluorogenic substrate (p-tosyl-Gly-Pro-Arg)2-rhodamine 110 (Invitrogen). This substrate contains the amino acid sequence recognized by α-thrombin, which is a peptidase. Thrombin cleavages the amino acid releasing the fluorescent rhodamine. During the test, it was measured the increase in fluorescence over time. The more enzyme activity of α-thrombin higher the cleavage speed, and therefore the release of rhodamine, which causes the increase in fluorescence. FIG. 3 shows that the WT human recombinant prethrombin-2 (a) is less stable than the mutant human recombinant prethrombin-2 discloses in the present invention (b). The test with mutated recombinant prethrombin-2 of the invention shows no increase in fluorescence for 15 h (55 000 sec). This implies that in preparation of mutated recombinant prethrombin-2 of the invention there are not residues of active α-thrombin, neither are being produced during the time that test takes place. On the other hand, the test with WT human recombinant prethrombin-2 displays an increase in the fluorescence from the beginning of the test. This increase in fluorescence indicates the presence of active α-thrombin in the preparation; even though WT human recombinant prethrombin-2 was also obtained by genetic engineering in E. coli. Therefore the stability in vitro shown by mutant human prethrombin of present invention was due to the mutagenesis operated herein.

Example 4

α-Thrombin Activity Assays

In order to verify whether human α-thrombin could cleave mutated recombinant human and mouse prethrombins-2, were incubated both mutated recombinant proteins with WT human α-thrombin (Sigma Aldrich) in the presence of the fluorogenic substrate (p-tosyl-Gly-Pro-Arg)2-rhodamine 110 (Invitrogen). Thrombin activity assays were performed in a Varioskan Flash microplate reader (Thermo Scientific) using black microwell plates at room temperature. Samples (100 μl final volume) were incubated in 50 mM Tris-HCl, pH 9.0, 150 mM NaCl with $4 \times 10^{-6}$ M rhodamine 110, bis-(p-tosyl-L-glycyl-L-prolyl-L-arginine amide) (Invitrogen) and the fluorescence of the resulting solution was monitored using λexcitation=498 nm and λemission=521 nm.

The results obtained from the experiment display that in the presence of WT human α-thrombin, the protease activity increased considerably with time (FIG. 4, curves a, b), compared to the samples where only WT α-thrombin was added (FIG. 4, curve c). On the other hand, in the absence of WT α-thrombin, both mutants did not present enzymatic activity (FIG. 4, curves d, e), demonstrating their stability under the experimental conditions. These results clearly indicate that WT α-thrombin is able to cleavage both mutant recombinant prethrombins-2 to generate active enzymes with α-thrombin activity. Exogenous α-thrombin activates the mutant recombinant prethrombin-2 converting it into endogenous α-thrombin which in turn cleaves other macromolecules of prethrombin-2 and the fluorogenic substrate in the course of this autocatalytic reaction.

Example 5

Mutant Prethrombin-2 Self-Replication Assays

Another experiment proved that generated endogenous α-thrombin is able to cleavage mutated recombinant prethrombin-2 to maintain the autocatalytic process. A solution of mutated prethrombin-2 was treated with α-thrombin immobilized on agarose. Mouse mutant prethrombin-2 was cleaved using Thrombin CleanCleave™ Kit (Sigma-Aldrich) as described in manufacturer's directions. The protein solution was then filtered through a 0.22 μm filter to eliminate any remaining. To investigate the autocatalytic reaction, $5.38 \times 10^{-9}$ M cleaved mouse mutant prethrombin-2 was mixed with and without $2.3 \times 10^{-7}$ M untreated mouse mutant prethrombin-2 and with the fluorogenic substrate (p-tosyl-Gly-Pro-Arg)2-rhodamine 110 (Invitrogen). Then, the evolution of the fluorescence intensity was monitored using λexcitation=498 nm and λemission=521 nm.

FIG. 5 shows that in the presence of the cleaved mutant prethrombin-2 and excess of the untreated mutant prethrombin-2 (FIG. 5 curve a), the fluorescence signal increased considerably in comparison with the sample where only the cleaved mutant prethrombin-2 was included (FIG. 5 curve b). The untreated mutant prethrombin-2 treated with the buffer solution used to wash α-thrombin on agarose demonstrated no activity (FIG. 5 curve c). Consequently, growth in the protease activity was not caused by exogenous ☐α-thrombin that could have detached from agarose. This experiment confirms the ability of endogenous α-thrombin derived from mutated prethrombin-2 to participate in the autocatalytic reaction.

Example 6

Detection of α-thrombin

Different concentrations of human α-thrombin (Sigma-Aldrich) were mixed with and without untreated $5.3 \times 10^{-7}$ M mouse mutant prethrombin-2 disclosed herein. The reactions were carried out in 50 mM Tris-HCl, pH 9.0, 150 mM NaCl with $4 \times 10^{-6}$ M rhodamine 110, bis-(p-tosyl-L-glycyl-L-prolyl-L-arginine amide) (Invitrogen) and the fluorescence of the resulting solution was monitored using λexcitation=498 nm and λemission=521 nm.

FIG. 6A shows evolution of the fluorescence intensities for varying amounts of human α-thrombin mixed with the fluorogenic substrate in the presence (FIG. 6 curves a-h) or absence (FIG. 6 curves i-p) of mutated prethrombin-2. The fluorescence intensities demonstrated exponential growth in the presence of the mutant, pointing to the autocatalytic character of the reaction. In such case calibration plots of the first derivative of fluorescence intensity with respect to time dF/dt, representing the rate of reaction after 2 hours, versus analyse concentration (FIG. 6B) are more informative that the conventional plots [26]. On the basis of the obtained calibration curves we calculated the detection limit of the systems operating without mutated prethrombin-2 (0.488 pM, S/N=3, n=3) and with the mutant (10 fM, S/N=3, n=3).

Example 7

Detection of Prothrombin in Human Plasma

The present invention displays the advantage of the amplified assay for prothrombin over a conventional non amplified quantification method (FIG. 7). Varying concentrations of pooled human plasma (Sigma-Aldrich) were mixed with $6 \times 10^{-8}$ M ecarin (Sigma-Aldrich) with or without $1.5 \times 10^{-6}$ M mouse mutant prethrombin-2. The reactions were carried out in 50 mM Tris-HCl, pH 9.0, 150 mM NaCl with $4 \times 10^{-6}$ M rhodamine 110, bis-(p-tosyl-L-glycyl-L-prolyl-L-arginine amide) (Invitrogen) and the fluorescence of the resulting solution was monitored using λexcitation=498 nm and λemission=521 nm.

The detection limits of amplified (7.7 pL, S/N=3, RSD=12%, n=3) and non amplified (710 pL, S/N=3, RSD=6%, n=3) assays were calculated according to the calibration plots (FIG. 7B) depicting dF/dt at fixed time of 60 min versus volume of human plasma per microplate well. Taking into consideration that human plasma usually contains 90 μg/ml of prothrombin [27] the assay with autocatalytic amplification allowed to detect as low as 0.693 pg of prothrombin per microplate well. The conventional non amplified assay allowed to quantify as low as 63.9 pg of the analyte per well. Thus, employment of autocatalytic amplification cascade allows diminishing the volume of human plasma needed for the prothrombin assay by two orders of magnitude.

BIBLIOGRAPHY

[1] J. H. Lawson, Semin. Thromb. Hemost. 2006, 32 Suppl 1, 98-110.

[2] J. K. Heffernan, R. A. Ponce, L. A. Zuckerman, J. P. Volpone, J. Visich, E. E. Giste, N. Jenkins, D. Boster, S. Pederson, G. Knitter, T. Palmer, M. Wills, R. J. Early, M. C. Rogge, Regul. Toxicol. Pharmacol. 2007, 47, 48-58.

[3] M. F. Doyle, K. G. Mann, J. Biol. Chem. 1990, 265, 10693-10701.

[4] E. E. DiBella, M. C. Maurer, H. A. Scheraga, J. Biol. Chem. 1995, 270, 163-169.

[5] H. Yonemura, T. Imamura, K. Soejima, Y. Nakahara, W. Morikawa, Y. Ushio, Y. Kamachi, H. Nakatake, K. Sugawara, T. Nakagaki, C. Nozaki, J. Biochem. 2004, 135, 577-582.

[6] B. Potzsch, S. Hund, K. Madlener, C. Unkrig, G. Muller-Berghaus, Thromb. Res. 1997, 86, 373-383.

[7] K. Fujikawa, E. W. Davie, in Methods in Enzymology, Vol. 45, 1976, pp. 89-95.

[8] L. Zhu, R. Yang, J. Zhai, C. Tian, Biosens. Bioelectron. 2007, 23, 528-535.

[9] H. Nakamura, Y. Mogi, T. Akimoto, K. Naemura, T. Kato, K. Yano, I. Karube, Biosens. Bioelectron. 2008, 24, 455-460.

[10] A. Virel, L. Saa, V. Pavlov, Anal. Chem. 2009, 81, 268-272.

[11] L. Pollegioni, L. Piubelli, G. Molla, Febs J. 2009, 276, 6857-6870.

[12] L. Caseli, A. C. Perinotto, T. Viitala, V. Zucolotto, O. N. Oliveira, Langmuir 2009, 25, 3057-3061.

[13] R. M. Lequin, Clin. Chem. 2005, 51, 2415-2418.

[14] D. L. Bates, Trends Biotechnol. 1987, 5, 204-209.

[15] B. Shlyahovsky, V. Pavlov, L. Kaganovsky, I. Willner, Angew. Chem. Int. Ed. Engl. 2006, 45, 4815-4819.

[16] A. R. Khan, M. N. James, Protein Sci. 1998, 7, 815-836.

[17] C. J. Gadgil, B. D. Kulkarni, AIChE J. 2009, 55, 556-562.

[18] J.-W. Wu, Y. Wu, Z.-X. Wang, Eur. J. Biochem. 2001, 268, 1547-1553.

[19] D. Barrett, Biochem. J. 1970, 117, 57-59.

[20] Y. Weizmann, Z. Cheglakov, V. Pavlov, I. Willner, Angew. Chem. Int. Ed. Engl. 2006, 45, 2238-2242.

[21] Y. Weizmann, Z. Cheglakov, V. Pavlov, I. Willner, Nat. Protoc. 2006, 1, 554-558.

[22] S. P. Leytus, W. L. Patterson, W. F. Mangel, Biochem. J. 1983, 215, 253-260.

[23] M. K. Ramjee, Anal. Biochem. 2000, 277, 11-18.

[24] J. Y. Chang, Eur. J. Biochem. 1985, 151, 217-224.

[25] K. Soejima, N. Mimura, H. Yonemura, H. Nakatake, T. Imamura, C. Nozaki, J. Biochem. 2001, 130, 269-277.

[26] L. Saa, A. Virel, J. Sanchez-Lopez, V. Pavlov, Chem. Eur. J. 2010, 16, 6187-6192.

[27] J. A. Rob, S. Tollefsen, L. Helgeland, Anal. Biochem. 1997, 245, 222-225.

The invention claimed is:

1. A mutant prethrombin-2 comprising (a) the polypeptide sequences SEQ ID NO: 1 or SEQ ID NO: 2 or (b) polypeptides encoded by SEQ ID NO: 5 or SEQ ID NO: 6.

2. The mutant prethrombin-2 according to claim 1 comprising (a) the polypeptide sequence SEQ ID NO: 2 or (b) polypeptide encoded by SEQ ID NO: 6.

3. The mutant prethrombin-2 according to claim 1 characterized by having autocatalytic activity.

4. A method for preparing α-thrombin which comprises the following steps:

(a) modifying a DNA sequence encoding for a factor Xa cleavage site represented by SEQ ID NO:17 in wild type prethrombin-2 gene represented by SEQ ID NO:7 or SEQ ID NO:8 to a DNA sequence encoding for an α-thrombin cleavage site represented by SEQ ID NO:18;

(b) inserting a mutated DNA prethrombin-2 of step (a) into an expression vector;

(c) transforming a host cell with the expression vector of step (b);

(d) culturing the transformed host cell in an appropriate culture medium;

(e) harvesting the transformed host cell and solubilizing proteins in inclusion bodies;

(f) purifying mutant prethrombin-2;

(g) contacting the purified mutant prethrombin-2 obtained with α-thrombin; and (h) purifying the α-thrombin.

5. The method according to claim 4 wherein the expression vector is a plasmid.

6. The method according to claim 5 wherein the plasmid is pET-TEV-prethr-2 plasmid or pQE9-hprethr-2 plasmid.

7. The method according to claim 4 wherein the host cell is selected from the group consisting of bacterial cells, animal cells, and yeast.

8. The method according to claim 7 wherein the bacterial host cell is *E. coli.*

9. The method according to claim 7 wherein the host cell is yeast selected from the group consisting of *Saccharomyces* sp and *Pichia pastoris.*

10. The method according to claim 4 wherein the purification of α-thrombin comprises at least one step of affinity chromatography.

11. A kit for detecting α-thrombin/prothrombin in a sample comprising the mutant prethrombin-2 of claim 1, and instructions for use thereof.

12. The method according to claim 8 wherein the bacterial host cell is *E. coli* XL1-blue or *E. coli* BL21.

13. The mutant prethrombin-2 of claim 3, wherein the autocatalytic activity is located at the alpha-thrombin cleavage site represented by the amino acid sequence SEQ ID NO:18.

14. The mutant prethrombin-2 according to claim 3, characterized by being stable in vitro.

* * * * *